United States Patent [19]

Diehr et al.

[11] Patent Number: 4,956,356
[45] Date of Patent: Sep. 11, 1990

[54] PESTICIDAL 3-SUBSTITUTED 1-NITRO-2-IMINO-1,3-DIAZACYCLOALKANES

[75] Inventors: Hans-Joachim Diehr, Wuppertal; Benedikt Becker, Mettmann, both of Fed. Rep. of Germany

[73] Assignee: Bayer Aktiengesellschaft, Leverkusen, Fed. Rep. of Germany

[21] Appl. No.: 354,645

[22] Filed: May 19, 1989

[30] Foreign Application Priority Data

May 28, 1988 [DE] Fed. Rep. of Germany ....... 3818163

[51] Int. Cl.$^5$ .................. C07D 401/06; A61K 31/44
[52] U.S. Cl. ................................ 514/341; 514/378; 514/362; 514/397; 514/365; 514/275; 514/255; 548/247; 548/134; 548/248; 548/336; 548/202; 544/331; 544/405
[58] Field of Search ...................... 546/278; 514/341

[56] References Cited

U.S. PATENT DOCUMENTS 3,993,648 11/1976 Powell ................................ 544/54
4,297,496 10/1981 Davis et al. ......................... 544/332
4,803,277 2/1989 Shiokawa et al. .................. 546/275

FOREIGN PATENT DOCUMENTS 0192060 8/1986 European Pat. Off. .

OTHER PUBLICATIONS

Shiokawa et al., CA 110:8210d.
Chemical Abstracts, vol. 51, Feb. 10, 1957, No. 3.
Chemical Abstracts, vol. 54, Nov. 10, 1960, No. 21.
Chemical Abstracts, vol. 110, Jan. 2, 1989, No. 1.
Chemical Abstracts, vol. 109, Dec. 19, 1988, No. 25, No. 224736b.
Chemical Abstracts, vol. 109, Dec. 19, 1988, No. 25, No. 224737c.

Primary Examiner—Jane T. Fan
Attorney, Agent, or Firm—Sprung Horn Kramer & Woods

[57] ABSTRACT

Pesticidal 3-substituted 1-nitro-2-imino-1,3-diazacycloalkanes of the formula

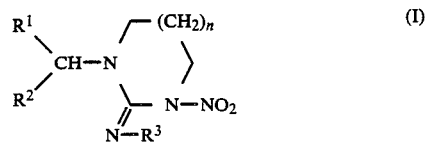

in which
n stands for the numbers 0 or 1,
$R^1$ stands for a five- or six-membered heterocyclic group which contains 1, 2, 3 or 4 nitrogen atoms and/or one or two oxygen atoms or sulphur atoms as hetero atom ring members—the number of the hetero atoms being 1, 2, 3 or 4—and which is optionally substituted by halogen, cyano, nitro, alkyl, halogenoalkyl, alkenyl, halogenoalkenyl, alkinyl, alkoxy, halogenoalkoxy, alkenyloxy, halogenoalkenyloxy, alkinyloxy, alkylthio, halogenoalkylthio, alkenylthio, halogenoalkenylthio, alkinylthio, alkylsulphinyl, halogenoalkylsulphinyl, alkylsulphonyl, halogenoalkylsulphonyl, amino, alkylamino, dialkylamino, aryl, aryloxy, arylthio, arylamino, aralkyl, formylamino, alkylcarbonylamino, formyl, carbamoyl, alkylcarbonyl and/or alkoxycarbonyl,
$R^2$ stands for hydrogen or alkyl and
$R^3$ stands for hydrogen or nitro.

7 Claims, No Drawings

PESTICIDAL 3-SUBSTITUTED 1-NITRO-2-IMINO-1,3-DIAZACYCLOALKANES

The present invention relates to new 3-substituted 1-nitro-2-imino-1,3-diazacycloalkanes, processes for their preparation, and their use as pesticides, in particular insecticides.

It has already been disclosed that certain organic nitro compounds, such as, for example, 2-nitromethylene-2H-tetrahydro-1,3-thiazine, exhibit insecticidal properties (cf. U.S. Pat. 3,993,648).

The new 3-substituted 1-nitro-2-imino-1,3-diazacycloalkanes of the general formula (I)

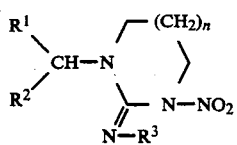

in which
n stands for the numbers 0 or 1,
$R^1$ stands for a five- or six-membered heterocyclic group which contains 1, 2, 3 or 4 nitrogen atoms and/or one or two oxygen atoms or sulphur atoms as hetero atom ring members—the number of the hetero atoms being 1, 2, 3 or 4—and which is optionally substituted by halogen, cyano, nitro, alkyl, halogenoalkyl, alkenyl, halogenoalkenyl, alkinyl, alkoxy, halogenoalkoxy, alkenyloxy, halogenoalkenyloxy, alkinyloxy, alkylthio, halogenoalkylthio, alkenylthio, halogenoalkenylthio, alkinylthio, alkylsulphinyl, halogenoalkylsulphinyl, alkylsulphonyl, halogenoalkylsulphonyl, amino, alkylamino, dialkylamino, aryl, aryloxy, arylthio, arylamino, aralkyl, formylamino, alkylcarbonylamino, formyl, carbamoyl, alkylcarbonyl and/or alkoxycarbonyl,
$R^2$ stands for hydrogen or alkyl and
$R^3$ stands for hydrogen or nitro,
have now been found.

The new 3-substituted 1-nitro-2-imino-1,3-diazacycloalkanes of the general formula (I) are obtained when
(a) 1-substituted 2-imino-1,3-diaza-cycloalkanes of the general formula (II)

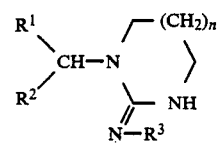

in which
n, $R^1$, $R^2$ and $R^3$ have the abovementioned meanings,
—or their hydrochlorides are— are reacted with a nitrating agent, if appropriate in the presence of a catalyst and if appropriate in the presence of a diluent, or when
—in the event that $R^3$ stands for hydrogen—
(b) 1-substituted 2-nitroimino-1,3-diazacycloalkanes of the general formula (IIa)

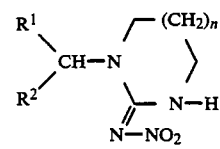

in which
n, $R^1$ and $R^2$ have the abovementioned meanings, are isomerized, if appropriate in the presence of a catalyst and if appropriate in the presence of a diluent.

The new 3-substituted 1-nitro-2-imino-1,3-diazacycloalkanes of the general formula (I) are distinguished by a powerful insecticidal activity.

Surprisingly, the compounds of the formula (I) according to the invention show a considerably more powerful insecticidal action than organic nitro compounds which have a similar structure and range of action, such as, for example, 2-nitromethylene-2H-tetrahydro-1,3-thiazine.

The invention preferably relates to compounds of the formula (I) in which
n stands for the numbers 0 or 1,
$R^1$ stands for a five- or six-membered heterocyclic group from the series comprising furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-,1,2,5- or 1,3,4-thiadiazolyl, pyridyl, pyrazinyl, pyrimidinyl and pyrazinyl, which group is optionally substituted by fluorine, chlorine, bromine, iodine, cyano, nitro, $C_1$–$C_4$-alkyl (which is optionally substituted by fluorine and/or chlorine), $C_2$–$C_4$-alkenyl (which is optionally substituted by fluorine and/or chlorine), $C_2$–$C_4$-alkinyl, $C_1$–$C_4$-alkoxy (which is optionally substituted by fluorine and/or chlorine), $C_3$–$C_4$-alkenyloxy (which is optionally substituted by fluorine and/or chlorine), $C_3$–$C_4$-alkinyloxy, $C_1$–$C_4$-alkylthio (which is optionally substituted by fluorine and/or chlorine), $C_3$–$C_4$-alkenylthio (which is optionally substituted by fluorine and/or chlorine), $C_3$–$C_4$-alkinylthio, $C_1$–$C_4$-alkylsulphinyl (which is optionally substituted by fluorine and/or chlorine), $C_1$–$C_4$-alkylsulphonyl (which is optionally substituted by fluorine and/or chlorine), amino, $C_1$–$C_4$-alkylamino, di-($C_1$–$C_4$-alkyl)-amino, phenyl, phenoxy, phenylthio, phenylamino, benzyl, formylamino, $C_1$–$C_4$-alkylcarbonylamino, formyl, carbamoyl, $C_1$–$C_4$-alkylcarbonyl and/or $C_1$–$C_4$-alkoxy-carbonyl,
$R^2$ stands for hydrogen or $C_1$–$C_3$-alkyl and
$R^3$ stands for hydrogen or nitro.

The invention particularly relates to compounds of the formula (I) in which
n stands for the numbers 0 or 1,
$R^1$ stands for a five- or six-membered heterocyclic group from the series comprising pyrazolyl, 1,2,4-triazolyl, oxazolyl, isoxazolyl, thiazolyl, isothiazolyl, 1,2,5-thiadiazolyl, pyridyl, pyrazinyl and pyrimidinyl, which group is optionally substituted by fluorine, chlorine, bromine, cyano, nitro, $C_1$–$C_2$-alkyl (which is optionally substituted by fluorine and/or chlorine), $C_1$–$C_2$-alkoxy (which is optionally substituted by fluorine and/or chlorine), $C_1$–$C_2$-alkylthio (which is optionally substituted by fluorine and/or chlorine) or $C_1$–$C_2$-alkylsulphonyl (which is optionally substituted by fluorine and/or chlorine),
R² stands for hydrogen and
R³ stands for hydrogen or nitro.

If, for example, 1-(2-chloro-thiazol-5-yl-methyl)-2-nitroiminoimidazolidine and nitric acid are used as starting substances, the course of the reaction in process (a) according to the invention can be outlined by the following equation:

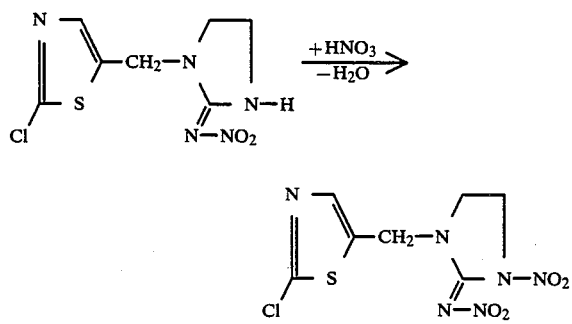

If likewise 1-(2-chloro-thiazol-5-yl-methyl)-2-nitroiminoimidazolidine is used as the starting substance, the course of the reaction in process (b) according to the invention can be outlined by the following equation:

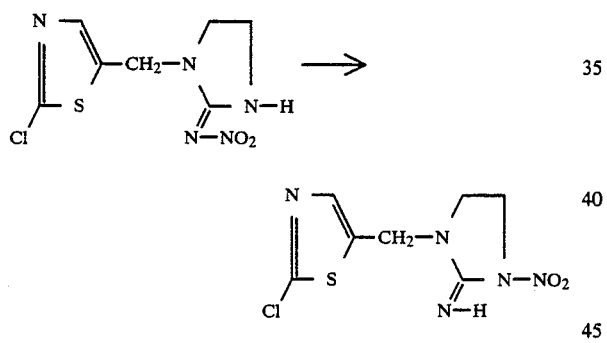

Formula (II) provides a general definition of the 1-substituted 2-imino-1,3-diaza-cyclo-alkanes to be used as starting substances in process (a) according to the invention for the preparation of compounds of the formula (I).

In the formula (II), n, R¹, R² and R³ preferably, or in particular, have those meanings which have already been mentioned above in connection with the description of the compounds of the formula (I) according to the invention as being preferred, or particularly preferred, for n, R¹, R² and R³.

Examples of the starting substances of the formula (II) are listed in Table 1 below.

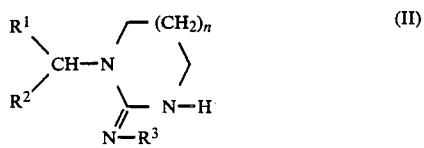

TABLE 1

Examples of starting substances of the formula (II)

| n | R¹ | R² | R³ |
|---|---|---|---|
| 0 | ![pyridyl] | H | H |
| 0 | Cl-pyridyl | H | H |
| 0 | Cl-thiazolyl | H | H |
| 1 | pyridyl | H | H |
| 1 | Cl-pyridyl | H | H |
| 1 | Cl-thiazolyl | H | H |
| 0 | Cl-pyridyl | H | NO₂ |
| 0 | pyridyl | H | NO₂ |
| 0 | N-methyl-pyrazolyl | H | H |
| 0 | CH₃-isoxazolyl | H | NO₂ |
| 0 | CH₃-oxazolyl | H | H |
| 0 | CH₃-thiazolyl | H | H |
| 0 | F-pyridyl | H | H |

TABLE 1-continued

Examples of starting substances of the formula (II)

| n | R¹ | R² | R³ |
|---|---|---|---|
| 1 | 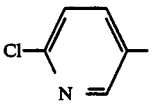 | H | NO₂ |
| 0 | 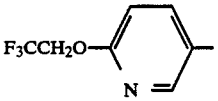 | H | H |
| 0 | 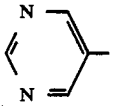 | H | H |
| 0 | 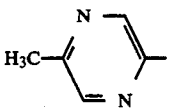 | H | H |
| 0 |  | H | H |
| 0 | 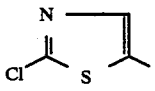 | H | NO₂ |
| 0 | 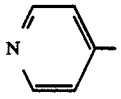 | H | NO₂ |
| 1 | 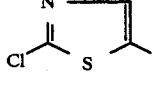 | H | NO₂ |
| 0 | 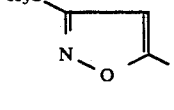 | H | H |
| 1 | 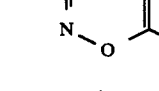 | H | NO₂ |
| 0 | 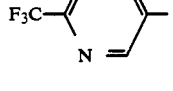 | H | H |
| 0 | 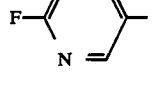 | H | NO₂ |
| 0 | 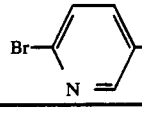 | H | H |

Formula (IIa) provides a general definition of the 1-substituted 2-nitroimino-1,3-diaza-cycloalkanes to be used as starting substances in process (b) according to the invention for the preparation of compounds of the formula (I).

In formula (IIa), n, R¹ and R² preferably, or in particular, have those meanings which have already been mentioned above in connection with the description of the compounds of the formula (I) according to the invention as being preferred, or particularly preferred, for n, R¹ and R².

Examples of the starting substances of the formula (IIa) can be seen from Table 1 (R³ is NO₂).

The starting substances of the formulae (II) and (IIa) are known and/or can be prepared by processes known per se (cf. EP-A No. 192,060).

Process (a) according to the invention is carried out using a nitrating agent. The usual substances which are suitable for nitrating organic compounds can be used. Nitric acid is preferably used as a nitrating agent.

Processes (a) and (b) according to the invention are preferably carried out in the presence of a catalyst. Suitable catalysts are acids, such as sulphuric acid, methanesulphonic acid or acetic acid, acid anhydrides, such as acetic anhydride, and/or salts of transition metals, such as copper sulphate or copper nitrate. Preferably, sulphuric acid is used as the catalyst.

Processes (a) and (b) according to the invention are preferably carried out in the presence of a diluent. Suitable diluents are acid anhydrides, such as, for example, acetic anhydride, acids, such as sulphuric acid, methanesulphonic acid or acetic acid, and inert organic solvents, such as methylene chloride, and also water.

In processes (a) and (b) according to the invention, the reaction temperatures can be varied within a relatively wide range. In general, the process is carried out at temperatures between −20° C. and +80° C., preferably at temperatures between 0° C. and 50° C.

Processes (a) and (b) according to the invention are generally carried out under atmospheric pressure. However, it is also possible for the processes to be carried out under increased or reduced pressure.

For carrying out process (a) according to the invention, between 1 and 5 moles, preferably between 1 and 2 moles, of a nitrating agent is generally employed per mole of starting compound of the formula (II).

In general, the reactants are mixed with slight cooling and are stirred at room temperature or slightly increased temperature until the reaction is complete. Work-up can be carried out by customary methods.

Apart from the nitrating agent, process (b) according to the invention can be carried out in the same manner as process (a).

The active compounds are suitable for combating animal pests, preferably arthropods, in particular insects, encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*
From the order of the Diplopoda, for example, *Blaniulus guttulatus.* From the order of the Chilopoda, for example, *Geophilus carpophagus* and Scutigera spec.
From the order of the Symphyla, for example, *Scutigerella immaculata.* From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp.. From the order of the Anoplura, for example, *Phylloxera vastatrix,* Pemphigus spp., *Pediculus humanus corporis,* Haematopinus spp and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*. From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*. From the order of the Siphonaptera, for example, *Xenopsylla cheopis* and Ceratophyllus spp. From the order of the Arachnida, for example, Scorpio maurus and Latrodectus mactans.

The compounds of the formula (I) according to the invention are distinguished by an excellent insecticidal activity. They show a powerful action, in particular when applied against insects which are harmful to plants, in particular against aphids, but also against soil insects (root-systemic action).

Some of the compounds according to the invention also show a fungicidal action, for example against downy mildews and rice blast disease (Pyricularia oryzae).

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionogenic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxyl, chlorinated hydrocarbons, phenylureas and substances produced by microorganisms, and the like.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

PREPARATION EXAMPLES

Example 1

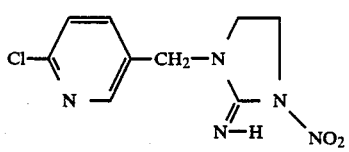

(Process a)

24.7 g (0.1 mol) of 1-(2-chloro-pyridin-5-yl-methyl)-2-imino-imidazolidine hydrochloride are suspended at 10° C. to 20° C. in 80 ml of 96% strength sulphuric acid. The hydrogen chloride which is liberated in this process is stripped off under a waterpump vacuum, and 10.3 g (0.16 mol) of 98% strength nitric acid are added at 10° C. to 20° C. to the resulting clear solution. The reaction mixture is stirred at 20° C. for 12 hours, mixed with ice, rendered neutral using sodium hydroxide solution and extracted using methylene chloride. The organic phase is washed with water, dried with sodium sulphate and filtered. The solvent is carefully distilled off from the filtrate under a waterpump vacuum.

21.3 g (83.5% of theory) of 1-(2-chloro-pyridin-5-yl-methyl)-2-imino-3-nitro-imidazolidine are obtained as an oily residue which crystallizes on scratching. Melting point: 81° C.

Example 2

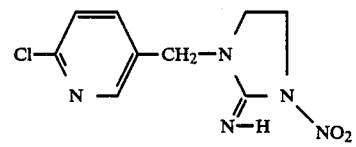

(Process b)

63.9 g (0.25 mol) of 1-(2-chloro-pyridin-5-yl-methyl)-2-nitroimino-imidazolidine are suspended at 20° C. to 25° C. in 250 ml of 96 % strength sulphuric acid—external cooling by ice water required. The reaction mixture is stirred at 20° C. for 12 hours and worked up as described in Example 1.

53.5 g (84 % of theory) of 1-(2-chloro-pyridin-5-yl-methyl)-2-imino-3-nitro-imidazolidine of melting point 81° C. are obtained.

Example 3

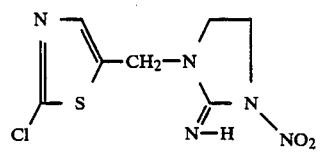

(Process a)

(a) In analogy to Example 1, 3.2 g (27% of theory) of 1-(2-chloro-thiazol-5-yl-methyl)-2-imino-3-nitro-imidazolidine of melting point 120° C. were obtained from 12.7 g (0.05 mol) of 1-(2-chloro-thiazol-5-yl-methyl)-2-iminoimidazolidine hydrochloride, 40 ml of 96% strength sulphuric acid and 5.1 g of 98% strength nitric acid.

(Process b)

(b) In analogy to Example 2, 5.2 g (40% of theory) of 1-(2-chloro-thiazol-5-yl-methyl)-2-imino-3-nitro-imidazolidine of melting point 120° C. were obtained from 13.1 g (0.05 mol) of 1-(2-chloro-thiazol-5-yl-methyl)-2-nitroiminoimidazolidine and 50 ml of 96% sulphuric acid.

Example 4

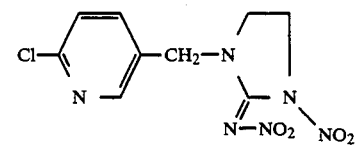

(Process a)

12.8 g (0.05 mol) of 1-(2-chloro-pyridin-5-yl-methyl)-2-nitroimino-imidazolidine are dissolved at 15° C. to 20° C. in 40 ml of glacial acetic acid. 4.8 ml of 98% strength nitric acid are first added at 20° C. to 25° C. to the solution, followed by dropwise addition of 14 ml of acetic anhydride. The reaction mixture is stirred at 20° C. for 150 minutes and then poured into ice water. The product obtained in the form of crystals is isolated by filtering off with suction.

13.1 g (87% of theory) of 1-(2-chloro-pyridin-5-yl-methyl)-2-nitroimino-3-nitro-imidazolidine of melting point 158° C. are obtained.

In analogy to Examples 1 to 4, the following compounds of the general formula

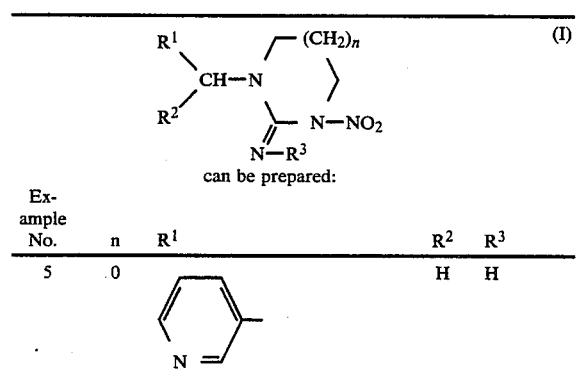

can be prepared:

| Example No. | n | R¹ | R² | R³ |
|---|---|---|---|---|
| 5 | 0 | 3-pyridyl | H | H |
| 6 | 1 | 3-pyridyl | H | H |
| 7 | 1 | 2-chloro-pyridin-5-yl | H | H |
| 8 | 1 | 2-chloro-thiazol-5-yl | H | H |
| 9 | 0 | 3-pyridyl | H | NO₂ |
| 10 | 0 | 1-methyl-pyrazol-3-yl | H | H |
| 11 | 0 | 3-methyl-isoxazol-5-yl | H | NO₂ |
| 12 | 0 | isoxazol-5-yl | H | H |
| 13 | 0 | 2-methyl-thiazol-5-yl | H | H |
| 14 | 0 | 2-fluoro-pyridin-5-yl | H | H |
| 15 | 1 | 2-chloro-pyridin-5-yl | H | NO₂ |
| 16 | 0 | 2-(2,2,2-trifluoroethoxy)-pyridin-5-yl | H | H |
| 17 | 0 | pyrimidin-5-yl | H | H |
| 18 | 0 | 2-methyl-pyrimidin-5-yl | H | H |
| 19 | 0 | 1,2,4-thiadiazol-3-yl | H | H |
| 20 | 0 | 2-chloro-thiazol-5-yl | H | NO₂ |
| 21 | 0 | 3-pyridyl | H | NO₂ |
| 22 | 1 | 2-chloro-thiazol-5-yl | H | NO₂ |
| 23 | 0 | 3-methyl-isoxazol-5-yl | H | H |
| 24 | 1 | 3-methyl-isoxazol-5-yl | H | NO₂ |
| 25 | 0 | 2-trifluoromethyl-pyridin-5-yl | H | H |
| 26 | 0 | 2-fluoro-pyridin-5-yl | H | NO₂ |

-continued $$\begin{array}{c} R^1 \\ \phantom{R^2}\diagdown \\ R^2 \diagup CH-N \diagup (CH_2)_n \\ \phantom{R^2 CH-N} \diagdown \\ \phantom{R^2 CH-N \diagdown} N-NO_2 \\ \phantom{R^2 CH-N \diagdown N} \phantom{-}N-R^3 \end{array} \quad (I)$$

can be prepared:

| Example No. | n | R¹ | R² | R³ |
|---|---|---|---|---|
| 27 | 0 | Br-pyridyl | H | H |

USE EXAMPLE

Example A

Myzus test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which have been heavily infested with the peach aphid (Myzus persicae) are treated by being dipped into the preparation of active compound of the desired concentration.

After the specified periods of time, the destruction in % is determined. 100% means that all the aphids have been killed; 0% means that none of the aphids have been killed.

In this test, for example the compound obtained in accordance with Preparation Examples 1 and 2 shows a superior activity compared with the prior art.

It will be understood that the specification and examples are illustrative but not limitative of the present invention and that other embodiments within the spirit and scope of the invention will suggest themselves to those skilled in the art.

We claim:

1. A 3-substituted 1-nitro-2-imino-1,3-imidazolidine of the formula $$\begin{array}{c} R^1 \\ \phantom{R^2}\diagdown \\ R^2 \diagup CH-N \\ \phantom{R^2 CH-N} \diagdown \\ \phantom{R^2 CH-N \diagdown} N-NO_2 \\ \phantom{R^2 CH-N \diagdown N} \phantom{-}N-R^3 \end{array}$$

in which
R¹ stands for pyridyl which group is optionally substituted by at least one of fluorine, chlorine, bromine, iodine, cyano, nitro, $C_1-C_4$-alkyl (which is optionally substituted by at least one of fluorine and chlorine), $C_2-C_4$-alkenyl (which is optionally substituted by at least one of fluorine and chlorine), $C_2-C_4$-alkinyl, $C_1-C_4$-alkoxy (which is optionally substituted by at least one of fluorine and chlorine), $C_3-C_4$-alkenyloxy (which is optionally substituted by at least one of fluorine and chlorine), $C_3-C_4$-alkinyloxy, $C_1-C_4$-alkylthio (which is optionally substituted by at least one of fluorine and chlorine), $C_3-C_4$-alkenylthio (which is optionally substituted by at least one of fluorine and chlorine), $C_3-C_4$-alkinylthio, $C_1-C_4$-alkylsulphinyl (which is optionally substituted by at least one of fluorine and chlorine), $C_1-C_4$-alkylsulphonyl (which is optionally substituted by at least one of fluorine and chlorine), amino, $C_1-C_4$-alkylamino, di-($C_1-C_4$-alkyl)-amino, phenyl, phenoxy, phenylthio, phenylamino, benzyl, formylamino, $C_1-C_4$-alkyl-carbonyl amino, formyl, carbamoyl, $C_1-C_4$-alkyl-carbonyl and $C_1-C_4$-alkoxy-carbonyl,
R² stands for hydrogen or $C_1-C_3$-alkyl and
R³ stands for hydrogen or nitro.

2. A 3-substituted 1-nitro-2-imino-1,3-imidazolidine according to claim 1, in which
R¹ stands for pyridyl which group is optionally substituted by fluorine, chlorine, bromine, cyano, nitro, $C_1-C_2$-alkyl (which is optionally substituted by at least one of fluorine and chlorine), $C_1-C_2$-alkoxy (which is optionally substituted by at least one of fluorine and chlorine), $C_1-C_2$-alkylthio (which is optionally substituted by at least one of fluorine and chlorine) or $C_1-C_2$ alkylsulphonyl (which is optionally substituted by at least one of fluorine and chlorine),
R² stands for hydrogen and
R³ stands for hydrogen or nitro.

3. A compound according to claim 1, wherein such compound is 1-(2-chloro-pyridin-5-yl-methyl)-2-imino-3-nitro-imidazoldine the formula $$\begin{array}{c} Cl-\text{pyridyl}-CH_2-N \\ \phantom{xxxxxxxxxxxxx} \diagdown \\ \phantom{xxxxxxxxxxxxx} C=N-H \\ \phantom{xxxxxxxxxxxxx} \diagup \\ \phantom{xxxxxxxxxxxxx} N-NO_2 \end{array}$$

4. A compound according to claim 1, wherein such compound is 1-(2-chloro-pyridin-5-yl-methyl)-2-nitroimino-3-nitroimidazolidine of the formula $$\begin{array}{c} Cl-\text{pyridyl}-CH_2-N \\ \phantom{xxxxxxxxxxxxx} \diagdown \\ \phantom{xxxxxxxxxxxxx} C=N-NO_2 \\ \phantom{xxxxxxxxxxxxx} \diagup \\ \phantom{xxxxxxxxxxxxx} N-NO_2 \end{array}$$

5. An insecticidal composition comprising an insecticidally effective amount of a compound according to claim 1 and a diluent.

6. A method of combating insects which comprises applying to such insects or to an insect habitat an insecticidally effective amount of a compound according to claim 1.

7. The method according to claim 6, wherein such compound is
1-(2-chloro-pyridin-5-yl-methyl)-2-imino-3-nitroimidazolidine,
1-(2-chloro-pyridin-5-yl-methyl)-2-nitroimino-3-nitro-imidazolidine.

* * * * *